US 6,607,300 B1

(12) United States Patent
Kleinerman

(10) Patent No.: US 6,607,300 B1
(45) Date of Patent: Aug. 19, 2003

(54) METHODS AND DEVICES FOR SENSING TEMPERATURE AND OXYGEN PRESSURE WITH A SINGLE OPTICAL PROBE

(76) Inventor: Marcos Y. Kleinerman, 215 Sunset Ave., Amherst, MA (US) 01002

(*) Notice: Subject to any disclaimer, the term of this patent is extended or adjusted under 35 U.S.C. 154(b) by 0 days.

(21) Appl. No.: 10/251,416

(22) Filed: Sep. 20, 2002

(51) Int. Cl.⁷ .............................. G01J 1/20; G01J 1/42; G01N 21/64; G01N 7/00
(52) U.S. Cl. ...................... 374/120; 374/121; 374/131; 250/483.1; 250/484.3; 436/136; 422/82.05; 422/82.13; 422/83
(58) Field of Search ................................ 374/120, 121, 374/161, 131, 130; 250/458.1, 459.1, 461.1, 483.1, 484.1; 436/136, 68, 172, 164; 422/82.05, 82.13, 83

(56) References Cited

U.S. PATENT DOCUMENTS

| 4,374,328 A | * | 2/1983 | Tekippe et al. |
| 4,378,496 A | * | 3/1983 | Brogardh et al. |
| 4,539,473 A | * | 9/1985 | Brogardh et al. |
| 4,569,570 A | * | 2/1986 | Brogardh et al. |
| 4,708,494 A | * | 11/1987 | Kleinerman |
| 4,729,668 A | * | 3/1988 | Angel et al. |
| 4,880,972 A | * | 11/1989 | Brogardh et al. |
| 5,186,046 A | * | 2/1993 | Gouterman et al. |
| 5,302,025 A | * | 4/1994 | Kleinerman |
| 5,304,809 A | * | 4/1994 | Wickersheim |
| 5,332,316 A | * | 7/1994 | Kleinerman |
| 5,499,313 A | * | 3/1996 | Kleinerman |
| 5,991,479 A | * | 11/1999 | Kleinerman |

* cited by examiner

Primary Examiner—Diego Gutierrez
Assistant Examiner—Gail Verbitsky

(57) ABSTRACT

Method and devices for measuring spot temperatures and surface temperature distributions using a luminophor, and method and devices for determining temperature-corrected oxygen or surface air pressure distributions using the same oxygen-sensitive luminophor. The luminophor is excited sequentially by a first light of wavelengths $\lambda_1$ and intensity $P_1$ and a second light of wavelengths $\lambda_v$ and intensity $P_T$, generating a first luminescence light of intensity $I_1$ and a second luminescence light of intensity $I_T$, respectively. The absorption of light of wavelength $\lambda_v$ is substantially temperature-dependent in such a manner that the ratio $(I_T \cdot P_1 / I_1 \cdot P_T)$ increases substantially in a known manner with increasing temperature, substantially independent of any oxygen pressure, and the oxygen pressure can be determined as a function of the luminescence decay time.

16 Claims, 3 Drawing Sheets

THERMALLY ACTIVATED FLUORESCENCE INTENSITY $I_f$ VS. INVERSE ABSOLUTE TEMPERATURE OF DMSO SOLUTIONS OF RHODAMINE 6G AND TWO OTHER DYES

US 6,607,300 B1

METHODS AND DEVICES FOR SENSING TEMPERATURE AND OXYGEN PRESSURE WITH A SINGLE OPTICAL PROBE

FIELD OF THE INVENTION

The present invention relates to methods and devices for the measurement of temperatures and air and oxygen pressures with a single paint, optical fiber or other probe, and more particularly to said methods and devices using photoluminescent probes.

BACKGROUND

The measurement of oxygen pressure using photoluminescent dyes has been known for decades. The 1971 U.S. Pat. No. 3,612,866 to Stevens describes a method for determining oxygen concentrations from the quenching of the photoluminescence of the hydrocarbon pyrene embedded in oxygen-permeable plastics. Bacon and Demas used polymer-immobilized ruthenium complexes with for the same purpose [*Anal. Chem.* 59, 2780–85 (1987)]. U.S. Pat. No. 4,810,655 to Khalil and Gouterman provide a historical background referencing work done up to about 1986, including but not limited to the use of these and other photoluminescent materials, notably platinum porphyrins, at the tip of optical fibers for measuring oxygen pressure in blood. U.S. Pat. No. 5,965,642 to Gouterman and Carlson update that account to about 1997 and also describe the use of oxygen-sensitive photoluminescent dyes as paints used for mapping air pressure distributions on aerodynamic surfaces in wind tunnel studies. All of the above references use photoluminescent indicators so characterized that, when excited by a pulse of light of microsecond or sub-microsecond duration and wavelength or wavelengths within their lowest energy electronic absorption band, they emit a luminescence light with a decay time $\tau_{ox}$ which decreases in a known manner with increasing oxygen pressure. The decrease $\tau_{ox}$ parallels the quenching effect of the oxygen pressure. If $\tau$ is the luminescence decay time in the absence of oxygen and $t_{ox}$ is the decay time in the presence of oxygen, then $\tau/\tau_{ox}=I_0/I_{ox}$, where $I_0$ is the luminescence intensity in the absence of oxygen and $I_{ox}$ is the lower luminescence intensity in the presence of oxygen.

There is a need, in a plurality of fields, to measure simultaneously or quasi-simultaneously (within one or a few seconds) both the temperature of an object or environment and a second parameter, physical or chemical. In most cases the main objective is to measure said second parameter, but its measurement is substantially affected by temperature. In clinical practice it is often necessary to measure both the oxygen pressure and the temperature of blood or a tissue with a fiber optic technique. A preferred method for measuring oxygen pressure is the use of an oxygen-sensitive photoluminescent dye. The dimensional constrains may require that the same probe be a temperature probe as well.

Demas et al. disclosed that the same ruthenium complexes used for measuring oxygen pressure can be used as temperature indicators [*Proc. SPIE*, 1796, 71–75 (1992)], but in order to use the complexes as temperature probes it was necessary to exclude oxygen from them. His work did not teach or anticipate a way to measure temperature while the probe luminescence was being simultaneously quenched by oxygen.

U.S. Pat. No. 6,303,386 to Klimant et al. describes a system for measuring both oxygen pressure and temperature using a probe having two sensing layers. One layer has an immobilized oxygen-sensing porphyrin. The other layer has an immobilized ruthenium complex for measuring temperature. Only the oxygen-sensing layer was permeable to oxygen. The arrangement required two light sources and associated optical filters, and two photodetectors and associated electronics.

The measurement of air pressure distributions on three dimensional aerodynamic test surfaces is one of the many applications of pressure-sensitive paints, and the preferred paint technology is still, to this date, based on the oxygen quenching of photoluminescence. One limitation of this technique is that the pressure readings are affected by temperature changes. If temperature gradients are relatively large over the test surface the prior art requires a temperature-sensitive paint in addition to the pressure-sensitive paint. In some applications where two or multiple parts of the body under study are subject to identical fields, for instance rotor blades in turbomachinery, one can separate the pressure-sensitive paint from the temperature-sensitive paint and perform independent measurements on the two paints, which requires two different sensor systems. In parts of the surface under study where both temperature and pressure readings are required on the same point, the two paints must be applied, one on top of the other. This, in addition to requiring two sensor systems, may introduce serious compatibility problems between the two paints, as one paint may interfere with the measurements performed on the other.

Prior art temperature sensing techniques for moving objects like rotor blades use a luminescent paint applied to the object and having a temperature-dependent luminescence decay time $\tau_T$, which decreases in a known manner with increasing temperature as the luminescence quantum efficiency of the paint decreases. In order to get accurate data, the use of two sensing layers as in the prior art is subject to stringent requirements for the temperature sensing layer, as listed by Allison et al. "A Survey of Thermally Sensitive Phosphors for Pressure Sensitive Paint Applications", ISA Paper 472, May 2000. They are, inter alia:

1) Very uniform coatings;
2) The luminescence decay time $\tau_T$ must be shorter than 10 microseconds;
3) The luminescence should be excitable with a blue emitting diode (LED);
4) The luminescence spectrum should be different from that of the pressure sensing layer;
5) The luminescence of the phosphor should not excite the pressure sensing layer to luminesce.

These requirements could be relaxed, or even eliminated, if one could measure temperature and air pressure accurately and independently of each other, but with the same indicator. That would also greatly minimize the sources of error and greatly reduce the complexity of the measuring system.

There is a need, therefore, for a simple measuring system wherein the same oxygen-sensitive photoluminescent material used as a pressure probe can be used as a temperature probe. It is also desirable that the added temperature measurement on the pressure probe do not substantially increase the complexity of the pressure measuring system or require a different dedicated temperature measurement system.

One prior art system for measuring temperature, suitable for use with fiber optic techniques and referred to herein as the Thermally Activated Direct Absorption (TADA) system, is based on the direct measurement of a temperature-dependent optical absorption, using photoluminescent probes as the absorption indicators. The system is described in U.S. Pat. No. 5,499,313 to Kleinerman, which incorporates teachings from previous patents to Kleinerman. The system is suitable for measuring temperatures at any chosen point or at a multiplicity of points along which a long optical fiber probe is deployed, but it loses accuracy in temperature ranges within which the luminescence efficiency of the probe is substantially degraded. Furthermore, nothing in that patent or any other prior art teaches how to measure temperature and another physical or chemical variable with a photoluminescent indicator which is being simultaneously affected by both variables, or how to measure surface temperature distributions with a single indicator dispersed in a non-homogeneous coating.

OBJECTIVES OF THE INVENTION

It is the main object of the present invention to provide simple and inexpensive optical methods and instrumentation for measuring the temperature of objects or environments in the presence of other, simultaneously acting physical or chemical variables.

It is another object of the present invention to improve the TADA system so it can be used in temperature ranges within which the luminescence efficiency of the probe is substantially degraded.

It is a specific object of the present invention to provide simple and inexpensive methods and instrumentation whereby a single probe is used to measure both oxygen pressure and temperature essentially at the same time and independently of each other.

It is another object of the invention to provide improved systems for the optical measurement of diverse physical parameters while providing temperature compensation, using a single probe.

It is another object of the invention to provide better techniques for visualizing the air pressure and temperature distributions on the surfaces of solid bodies.

Yet another object of the invention is to provide new methods and devices for obtaining accurate measurement of surface temperature distributions using an indicator dispersed in a non-homogeneous paint, even if the indicator is being simultaneously affected by another distributed physical or chemical variable.

It is a further object of the invention to provide improved methods and devices for measuring localized temperatures and surface temperature distributions on fast moving bodies.

DEFINITIONS

Within the context of this application, I am using the following definitions:

Light: optical radiation, whether or not visible to the human eye.

$cm^{-1}$: energy units expressed as the inverse of the corresponding wavelength $\lambda$ when the wavelength is given in centimeters (cm).

Excitation light: illuminating light which can generate luminescence in a luminescent material.

Interrogating light: illuminating light injected into or incident on an optical probe for the physical variable.

Luminescence: Light emitted by a material upon absorption of light or other radiation of sufficient quantum energy. The term includes both fluorescence and phosphorescence.

Luminescence centers: atoms or molecules (including ions) of a photoluminescent material which absorb excitation light and emit luminescence light.

Luminescence decay time $\tau$: the time after the cessation of the excitation radiation in which the intensity of the luminescence decays from $I_o$ to $I_o/e$, where e is equal to 2.71828 and $I_o$ is the luminescence intensity at any reference time chosen as "zero" time.

Luminescence quantum efficiency $\phi$ (also referred to as luminescence efficiency): the ratio of the number of luminescence photons emitted by a luminescent material to the number of photons of the excitation light absorbed by the material.

Luminescence time rate of decay: the inverse of luminescence decay time $\tau$.

Single Luminophor: a photoluminescent material, whether pure, dissolved or dispersed in a polymer matrix, a glass or a paint, having a single light-emitting species, for example a specific platinum(I) porphyrin, or a specific ruthenium(II) complex with tris(4,7-diphenyl-1,10-phenanthroline), but not a composition containing both. Other example: $Nd^{3+}$ or other specific rare earth ion whether as a dopant or in a stoichiometric compound.

Occupancy number of an energy level: the fraction of the total number of molecules of a probe material occupying said energy level.

Paint: a relatively thin coating, whether or not colored, applied to an object as a sensing probe.

Photoluminescence: Luminescence generated by the absorption of light.

Physical variable: any physical (including chemical) property whose magnitude can change. Examples: pressure, temperature, flow rate, position, liquid level, oxygen and the like. (Synonims: measurand, physical parameter).

$\lambda_1$: wavelength of luminescence excitation light the optical absorption of which is not substantially affected by temperature.

$\lambda_v$: wavelength of luminescence excitation light the optical absorption of which is substantially temperature-dependent.

BRIEF SUMMARY OF THE INVENTION

The present invention improves and substantially extends the scope of the temperature measurement system based on the direct measurement of a temperature-dependent optical absorption by photoluminescent probes. That system, as described in section 2.1 of U.S. Pat. No. 5,499,313, and referred to herein as the Thermally Activated Direct Absorption (TADA) system, is based on a physical property shared by virtually all liquid or solid materials having an optical electronic absorption band in the visible or near infrared region of the optical spectrum. When these materials are illuminated with light of any wavelength or wavelengths $\lambda_v$ within the long wavelength tail of their lowest energy electronic absorption band, the magnitude of the fraction $\alpha$ of the intensity of the light which is absorbed is temperature-dependent, increasing in a known manner with increasing temperature. If these materials are photoluminescent, the luminescence intensity generated by the absorption of light of said wavelength or wavelengths $\lambda_v$ is also temperature-dependent, this intensity increasing in a manner directly proportional to the magnitude of $\alpha$ if the luminescence quantum efficiency of the photoluminescent material is not degraded over the temperature range of operation. A measurement of a luminescence intensity directly proportional to $\alpha$ is a direct measurement of light absorption, in contract to light transmission measurements, where the value of $\alpha$ is determined indirectly as a difference between two light intensities, not measured directly. U.S. Pat. No. 5,499,313 teaches how to measure temperature at any chosen point with a discrete sensor of known composition and thickness, and how to extend its main concept to the measurement of distributed temperatures by using a suitably doped long optical fiber probe.

The instant invention improves and substantially extends the TADA system so it can be used in temperature ranges within which the luminescence efficiency of the probe is substantially degraded.

Furthermore, the instant invention teaches new techniques for further extending the reach of the TADA system to allow a single photoluminescent probe material to be used for both temperature and oxygen and air pressure measurements, essentially simultaneously and independently of each other. Although they use the same probe, the measurements of temperature and of oxygen pressure do not interfere with each other when used according to the teachings of this invention. The reason there is no interference can be understood by noting that the oxygen quenching of the photoluminescence is a processes which occurs after the absorption of the excitation light, but the physical process indicative of the probe temperature is a light absorption process which occurs prior to the photoluminescence and is not, therefore, affected by any processes which affect the photoluminescence efficiency, provided that the photoluminescence intensity is measurable to the needed extent. This is an easily met requirement given the great sensitivity of light detectors for visible and near infrared radiation.

Now, a luminescence intensity generated by a temperature-dependent absorption of light of a given wavelength does depend on oxygen pressure, as this pressure affects the luminescence quantum efficiency in a manner that can easily be pre-determined. But this invention teaches how to make the temperature reading independent of luminescence quantum efficiency by referencing the temperature-dependent luminescence intensity to a luminescence intensity generated by absorbed light of a different pre-selected wavelength.

The technology subject of this invention can also be used for measuring temperature with any probe used for sensing concurrently any other physical or chemical measurand, provided the probe uses an efficient photoluminescent indicator, whether the indicator is unchanged, generated or partially consumed in the process.

The instant invention extends the capability of these techniques still further, by allowing the measurement of air pressure and temperature distributions over the surface of a body subject to these air pressure and temperature distributions. The invention permits these measurements with reasonably high accuracy using as sensors photoluminescent coatings even when the sensing points on the coatings are of non-uniform thickness and would, under the prior art techniques, generate many erroneous readings due to their different light absorption path lengths. The invention includes features for cancelling out the effects of these different thicknesses by performing measurements in two different wavelength regions and comparing the readings obtained from these two wavelength regions.

Still further, the instant invention makes it possible to measure accurately the surface temperatures of fast moving bodies, for example rotating turbine blades. In the prior art these measurements use as probes paints applied to the surface of said bodies, the paints including a photoluminescent material having a temperature-dependent luminescence decay time $\tau_T$. The measurements are carried out by exciting the luminescence of the paint with pulses of light of microsecond or sub-microsecond duration and measuring the luminescence decay time $\tau_T$. A serious disadvantage of this method is that, in a fast moving body one has to measure the intensities of two short duration fractions of the time-decaying luminescence from the illuminated spot. The first fraction is measured very shortly after the extinction of the excitation pulse, before the peak luminescence intensity has decayed significantly. The second fraction is measured a short interval afterwards, as the spot has moved rapidly away from the position where the intensity of its first luminescence portion was measured. Now, except for a relatively small group of materials described in Kleinerman's U.S. Pat. No. 5,222,810 section 2.0: Luminescent Materials Having two Emissive Levels with Temperature—Dependent Relative Populations, a decrease in the luminescence decay time $\tau$ of a probe with increasing temperature parallels a decrease in its luminescence efficiency, which inevitably decreases the signal-to-noise ratio of the measurement. In the high temperature region (above 500° C.) within which the luminescence decay time $\tau$ decreases appreciably per increasing degree the luminescence quantum efficiencies are often of the order of $10^{-2}$ or smaller. And since only a small fraction of the emitted luminescence intensity is measured, measurement accuracy is limited. The present invention overcomes these shortcomings and permits the measurement of temperatures and surface temperature distributions with photoluminescent probes which maintain their high luminescence efficiencies over their temperature range of operation and do not require a temperature-dependent change in their luminescence spectral distribution or luminescence efficiency.

PHYSICAL BASIS OF RELATED PRIOR ART

1. Thermally-activated Optical Absorption Processes in Photoluminescent and Other Materials The technology to be described uses the fact that all solid and liquid materials which absorb light of visible or near infrared wavelengths have a temperature-dependent optical absorption at the long wavelength tail of an electronic absorption band. If the materials are photoluminescent and absorb only a small fraction of the intensity of the incident light, the intensity of the photoluminescence is the most convenient indicator of the magnitude of the optical absorption. This can be understood with the help of FIG. 1. The analysis that follows, taken from Kleinerman's U.S. Pat. No. 5,499,313, is deliberately oversimplified to emphasize the aspects most relevant to the invention. The quantitative relationships may not be followed rigorously in all practical systems. I do not wish to be bound by theory, and the account that follows must be taken as a model for understanding how the absorption of light of some wavelengths by a material, and the luminescence intensity generated by the absorbed light, can increase substantially and predictably with increasing temperature.

Figure 1:
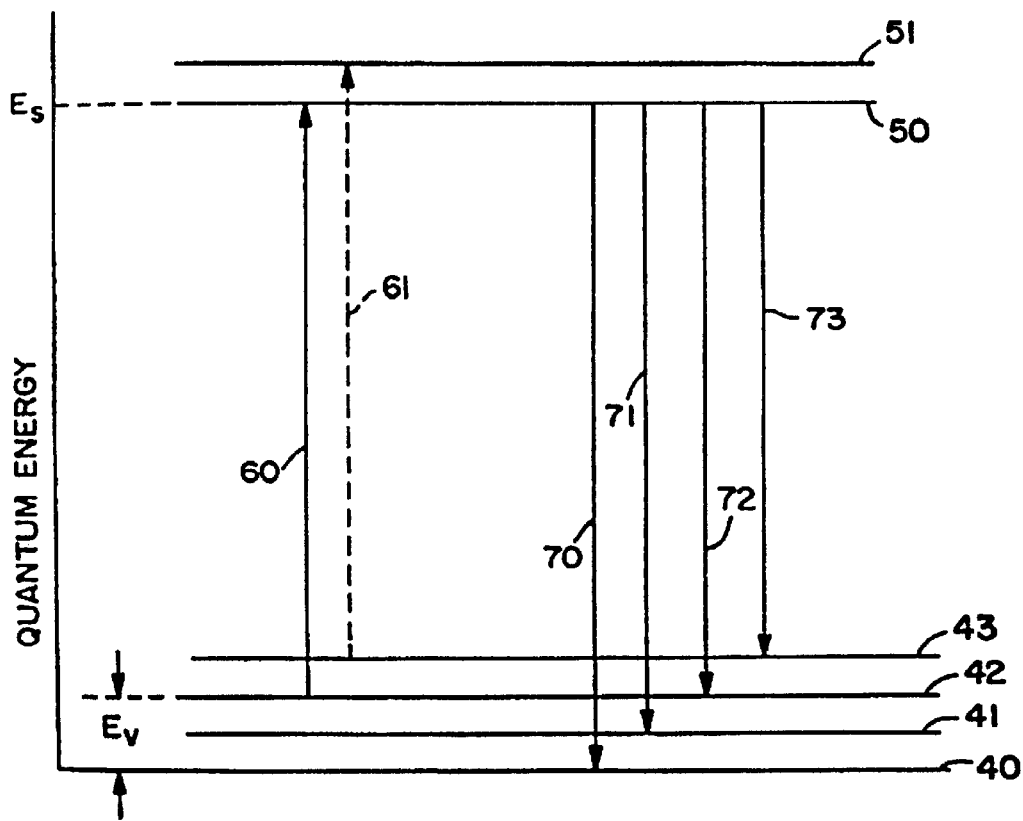
FIG. 1 is a simplified molecular energy diagram illustrating a temperature-dependent optical absorption process and luminescence conversion of the absorbed light in most photoluminescent materials.

FIG. 1 shows a diagram of electronic energy levels and transitions which at least qualitatively describes, at the molecular level, most luminescent materials. The luminescent material includes, at the atomic or molecular level, luminescence centers having a ground electronic level comprising vibrational sublevels 40, 41, 42, 43 and other sublevels which, for the sake of simplicity, are not shown.

The lowest excited electronic energy level comprises sublevels 50, 51, and any other sublevels not shown. The vertical arrowed line 60 represents an optical electronic transition produced by the absorbed excitation light from sub-level 42 to excited level 50, which have fixed energy levels $E_v$ and $E_s$, respectively, relative to the ground level 40 (The subscript "v" originated from the fact that in most photoluminescent materials the thermally excited sub-level is "vibronic"). The length of line 60 corresponds to the photon energy of the optical transition and, hence, to the specific wavelength $\lambda_v$ of the excitation light. This wavelength, usually in the long wavelength 'tail' of the electronic absorption band, obeys the relation $$\lambda_v = hc/(E_s - E_v) \text{ centimeters (cm)} \quad (1)$$

where h is Planck's constant and c is the velocity of light in free space. The wavelength $\lambda_v$ can excite only molecules occupying vibrational level 2 and, to a smaller extent, molecules occupying slightly higher levels, the excitation of which is represented by the dotted vertical line 61. Luminescence emission occurs from level 50 to the different sublevels of the ground electronic level, said emission represented by lines 70, 71, 72 and 73. As shown in FIG. 1, a considerable spectral portion of the emission occurs at photon energies higher (and wavelengths shorter) than that of the excitation light, and is commonly referred to as anti-Stokes emission.

In practice the photoluminescent material used in a temperature probe is usually a solid solution, glassy or crystalline, which constitutes the probe. The concentration of the photoluminescent material and the dimension of the probe along the direction of the interrogating light are chosen so that the probe absorbs only a temperature-dependent fraction $\alpha_T$ of the intensity of the nearly monochromatic excitation light within the temperature range of operation, and transmits the rest. At relatively low optical densities the fraction $\alpha_T$ of the intensity P of the interrogating light absorbed by the molecules occupying the sublevel 3 obeys the relation $$\alpha_T = KN_{42}/N_{40} \quad (2)$$

where $N_{42}$ is the number of molecules of the photoluminescent material occupying vibrational level 42;

$N_{40}$ is the number of the molecules of the photoluminescent material occupying level 42; and K is a constant specific to the probe Now $$N_{42}/N = \exp(-E_v/kT) \quad (3)$$

At optical densities no greater than about 0.02 $\alpha$ is given approximately by $$\alpha_T = K \cdot \exp(-E_v/kT) \quad (4)$$

where k is the Boltzmann factor and T the absolute temperature in kelvins. At optical densities greater than 0.02 the relationship between $\alpha$ and the Boltzmann factor $\exp(-E_v/kT)$ becomes less linear, but equations (2) and (3) still hold, and the method can be used at high, low or intermediate optical densities.

The luminescence intensity $I_T$ generated by the interrogating light absorbed by the probe obeys the relation $$I_T = P_T \cdot \phi K \cdot \exp(-E_v/kT) \text{photons·sec}^{-1} \quad (5)$$

where $P_T$ is the intensity of the incident interrogating light, and $\phi$ is the luminescence quantum efficiency of the photoluminescent material.

Probes made from materials having high $\phi$ values can produce large signal-to-noise ratios even with optical densities lower than 0.01, provided that the optical system has at least a moderately high collection efficiency for the probe luminescence. Such efficiency is easily obtainable with state-of-the-art systems.

The temperature coefficient of the luminescence intensity follows approximately the relation $$(1/I_{T0})(dI_T/dT) = E_v/kT^2 = \beta/T^2 \text{deg}^{-1} \quad (6)$$

where $I_{T0}$ is the luminescence intensity at a chosen reference temperature. For example, a material with an energy $E_v$ of 1200 cm$^{-1}$ has a coefficient of about two percent per kelvin at an ambient temperature of 295 K. Equation (6) assumes that the luminescence quantum efficiency $\phi$ is substantially independent of temperature over the temperature range of application of the method.

Equations (4) to (6) show that the method of the preceding paragraphs requires only a temperature-dependent change in the optical absorption coefficient of the luminescent probe material at wavelengths corresponding to photon energies lower than the energy $E_s$ of the excited emissive level. This property is shared by virtually all luminescent materials. The method does not require any temperature-dependent changes in the luminescence quantum efficiency, spectral distribution or decay time $\tau$. Therefore, it can be implemented with most luminescent materials.

Experimental tests of equations (4) to (6) have been carried out with liquid solutions of three different dyes dissolved in dimethyl sulfoxide (DMSO). Two of the dyes, dye I and dye II are represented by the chemical structures

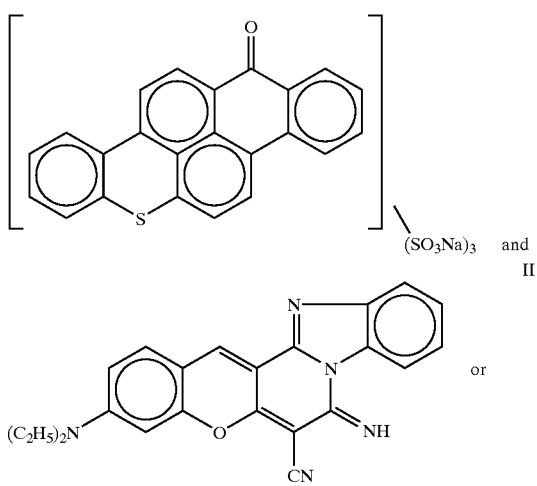

-continued

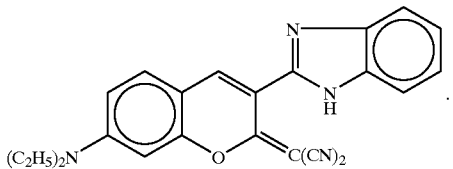

Figure 2:
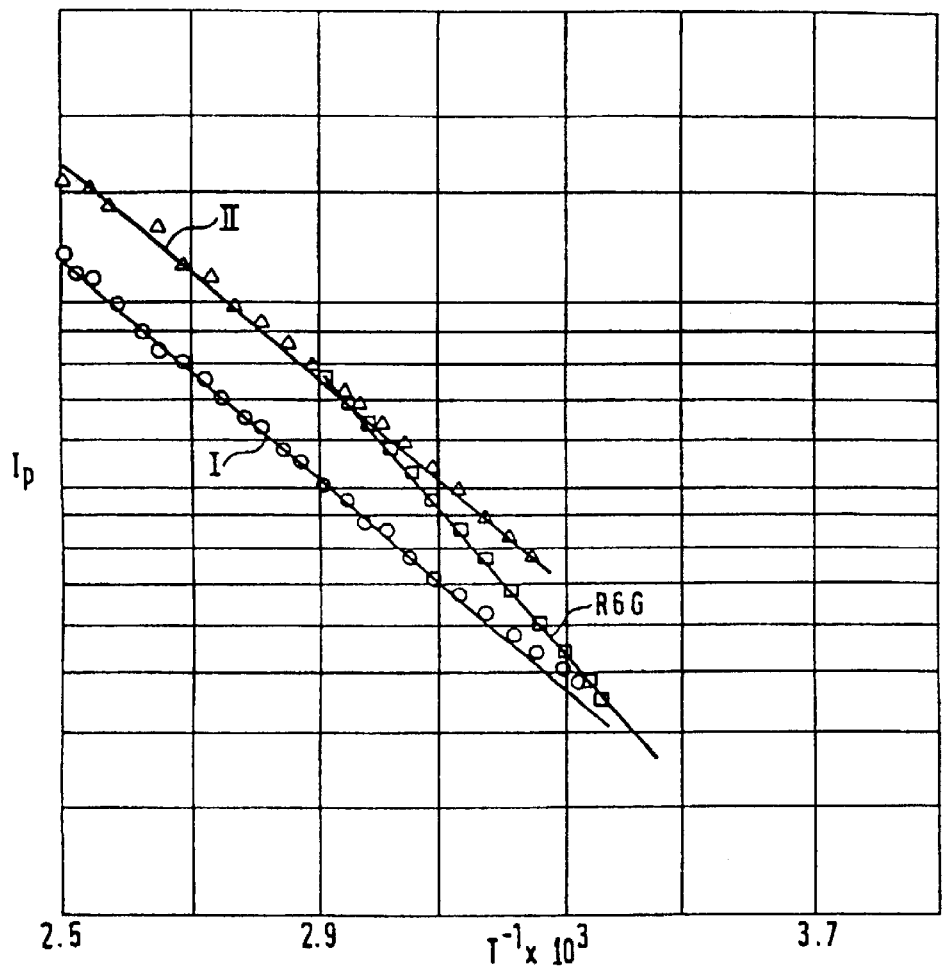
FIG. 2 shows the temperature dependence of the normalized thermally activated fluorescence intensities of three organic dyes as a function of the inverse absolute temperature.

Dye I is the sulfonated derivative of Hostasol Red GG (American Hoechst Corp.). Dye II has been described in U.S. Pat. No. 4,005,111 by Mach et. al. The third dye was the well known Rhodamine 6G (R6G). The dyes were dissolved in DMSO at concentrations of the order of $10^{-4}$ Molar and excited with light from a He—Ne laser ($\lambda_v$=633 nm) in a square cuvette. The fluorescence intensity was monitored at the wavelength of 612 nm, shorter than the wavelength of the excitation light. The experimentally measured fluorescence intensities $I_f$ were measured as a function of the absolute temperature T. Plots of $I_T$ v. $T^{-1}$ are shown in FIG. 2 for the three dyes. The behavior predicted by equations (3) and (5) was confirmed. The slopes of the lines drawn through the experimental points give $E_v$ values of 1380, 1355 and 1890 cm$^{-1}$ for dyes I, II and R6G, respectively. When these values are added to the excitation photon energy of 15803 cm$^{-1}$, one obtains $E_s$ values of $1.72 \times 10^4$ cm$^{-1}$ for dyes I and II, and $1.77 \times 10^4$ cm$^{-1}$ for R6G. These values are in good a with the $E_s$ values determined from the fluorescence spectra of these dyes.

Figure 3:
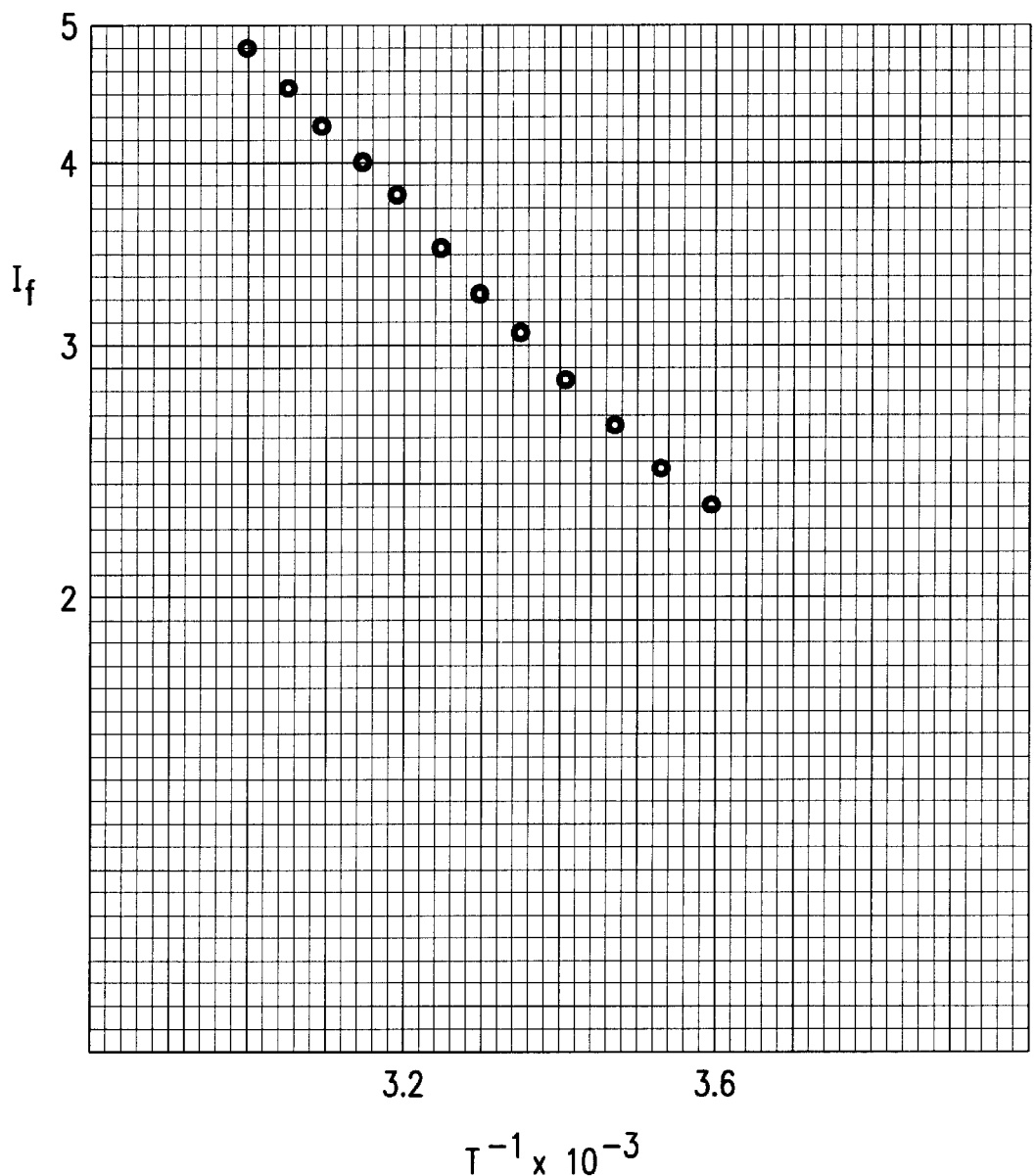
FIG. 3 shows the temperature dependence of the normalized thermally activated fluorescence intensity of a polymer solution of an organic dye as a function of the inverse absolute temperature.

Dye II was incorporated into a poly-α-methyl styrene plastic at a concentration of the order of 0.01 Molar. FIG. 3 shows the temperature dependence of its normalized fluorescence intensity $I_f$ over a temperature range of medical interest.

DETAILED DESCRIPTION OF THE INVENTION

2. Elimination of Luminescence Efficiency Effects in TADA Temperature Measurements The TADA method as described above is applicable for systems that use photoluminescent materials having an essentially constant luminescence quantum efficiency φ over the temperature range of application of the method. It is to be noted that derivation of equation (6) from equation (5) assumes that constancy. It is one of the main features of the instant invention that it extends the applicability of the TADA method to temperature ranges wherein the value of φ varies substantially, usually decreasing with increasing temperature.

The improved TADA method is based on the fact that, while the absorbed fraction $\alpha_T$ of the intensity of light of wavelength or wavelengths $\lambda_v$, in the long wavelength 'tail' of the electrinic absorption band, is substantially temperature-dependent and generates a luminescence of temperature-dependent intensity $I_T$, if the same material is excited with light of shorter wavelength or wavelengths $\lambda_1$ near the peak of the same electronic absorption band the absorbed fraction $\alpha_1$ of the light intensity has relatively little or no temperature dependence and generates a luminescence of intensity $I_1$ directly proportional to $\alpha_1$. The ratio $I_T/I_1$ of these intensities is an unambiguous temperature indicator independent of the value of φ, even if this value is temperature-dependent. This follows from the following analysis:

The luminescence intensity $I_1$ measured by a suitable photodetector follows the relation $$I_1 = P_1 \alpha_1 \phi \qquad (7)$$

The absorbed fraction $\alpha_T$ of the light of wavelength $\lambda_v$ follows equation (4), that is, $\alpha_T = K \cdot \exp(-E_v/kT)$. Therefore the luminescence intensity $I_T$ measured by a suitable photodetector (which can be either the same one used for measuring $I_1$ or a second photodetector) follows the relation $$I_T = P_T K \phi \exp(-E_v/kT) \qquad (8)$$

Since both excitation wavelengths are within the same absorption band the luminescence quantum efficiency φ is the same. Dividing $I_T$ by $I_1$ we get $$(I_T P_1/I_1 P_T) = (K/\alpha_1) \exp(-E_v/kT)$$

Now, writing A for $(K/\alpha_1)$ and solving for T one gets the relation $$T = A \cdot E_v/k \cdot \ln(I_T P_1/I_1 P_T) \qquad (9)$$

where A is a constant, ln is shorthand for naperian logarithm, and φ has been canceled out!

Whether or not equations (4)–(6) or (8) are rigorously obeyed by an actual system, the ratio $(I_T P_1/I_1 P_T)$ will be a reproducible and accurate temperature indicator, regardless of the oxygen pressure or any parameter that affects the quantum efficiency, spectral distribution or decay time τ of the generated luminescence.

3.—Measurement of Temperature and Oxygen Pressure with a Single Probe

The main feature of this invention is the ability to measure temperature and oxygen pressure, each independently of the measurement of the other, simultaneously or quasi-simultaneously (within one or a few seconds) using a single photoluminescent material as a probe for both parameters. The measurements can be independent of each other because oxygen pressure affects the luminescence decay time τ of the probe after the luminescence excitation light has been absorbed, independently of the wavelength of the excitation light, whereas the temperature measurement depends on a temperature-dependent light absorption property at a pre-selected wavelength before any luminescence light is emitted, independently of anything that affects the luminescence emission.

Now, the oxygen pressure reading does depend on temperature in a manner that can easily be pre-determined, but since the temperature readings can be made independent of the oxygen pressure, as shown below, any temperature effect on the oxygen pressure reading can be easily compensated to give a temperature-corrected reading.

For any specific oxygen photoluminescent probe based on the oxygen effect on the luminescence decay time τ one can determine, in a controlled experiment, the effect of varying oxygen pressure on the luminescence decay time τ of the probe at a given temperature. Then, for any known oxygen pressure one can vary the temperature in a controlled manner to obtain the temperature effect on the measured luminescence decay time τ, referenced to any chosen temperature. Once such data have been obtained and stored in memory, any oxygen pressure reading at any measured temperature can be temperature-corrected to obtain the true value of the oxygen pressure.

Equations (4) to (6) are at least approximately valid for all photoluminescent materials, so they apply to the ruthenium complexes and the platinum porphyrins mentioned above, which are popular oxygen sensing dyes.

3.1 Measurement of Spot Temperature and Oxygen Pressure

Spot measurements of oxygen pressure and temperature can be conveniently carried out with the oxygen sensor, for example a platinum porphyrin, immobilized in an oxygen-permeable matrix attached to the tip of an optical fiber. Before the measurements are carried out, the probe is calibrated as follows:

1. (a) A fluorescence spectral response curve is constructed for the probe and the optical system used, namely a plot of its fluorescence intensity $I_\lambda$ as a function of excitation wavelength at a reference temperature, normalized to a constant intensity for the excitation light, for a spectral region from just past the peak of its longest wavelength electronic absorption band to longer wavelengths within the tail of the band which can be absorbed only by molecules occupying a thermally excited level. Within this spectral region, two excitation light sources of narrow wavelength bands $\lambda_1$ and $\lambda_v$, respectively, are chosen so that the absorption of light of wavelengths $\lambda_1$ and intensity $P_1$ is independent or only minimally dependent on temperature and generates a relatively strong luminescence intensity $I_1$ with relatively little or no temperature dependence, and the light of wavelengths $\lambda_v$ and intensity $P_T$ is absorbed only by molecules occupying a thermally excited level of energy $E_v$ above the ground level, thus generating a luminescence intensity $I_T$ which has a strong temperature dependence consistent with a convenient signal-to-noise ratio. (The most suitable wavelengths $\lambda_1$ are usually at or near the peak of the lowest energy electronic absorption band. The wavelengths $\lambda_v$ are usually at or near the bottom of the long wavelength 'tail' of the same band).

(b) For each of the excitation lights of wavelengths $\lambda_1$ and $\lambda_v$ of intensities $P_1$ and $P_T$, respectively, construct a luminescence intensity $I_T$ vs. absolute temperature T plot for the temperature range of operation, other things being equal.

(c) For a constant (or normalized) intensity $P_1$ of the excitation light of wavelength $\lambda_1$, and at each temperature within a multiplicity of temperatures within the temperature range of operation, construct a plot of the luminescence decay time $\tau$ vs. oxygen pressure over the range of oxygen pressures to be measured. These plots are especially important if $\tau$ decreases in a known manner with increasing temperature as the luminescence quantum efficiency of the paint decreases.

Once the probe has been calibrated, the temperature being measured can be determined unambiguously from the ratio $(I_T P_1/I^1 P_T)$ as shown in section 2. The oxygen pressure can be determined from $\tau$. The measurement of a luminescence decay time is straightforward and well known to workers in the art having at least average competence. To the extent that $\tau$ may depend on temperature, the temperature obtained from the ratio $(I_T P_1/I_1 P_T)$ can be effectively used for providing a temperature compensation factor for the measured $t$ values.

Photoluminescent Materials Suitable for the Practice of this Invention

The technology subject of this invention for sensing both oxygen pressure and temperature with a single probe can be used with any photoluminescent material the luminescence of which is partially quenched by oxygen. Therefore, all photoluminescent materials used in the prior art as oxygen probes are suitable. The most widely used materials are ruthenium(II) complexes with tris(4,7-diphenyl-1,10-phenanthroline) and platinum porphyrins. Their current use is due perhaps more to technological inertia than to their instrumental suitability. They require excitation light sources in the green and yellow spectral regions, for which small inexpensive diode lasers are not yet available (although suitable LEDs are available). Small, efficient, inexpensive diode lasers are available in the red region for wavelengths from about 630 to about 690 nanometers (nm) and in the near infrared region. It should be advantageous to use oxygen-quenchable photoluminescent materials having absorption bands in these regions, especially for applications where the luminescence signals generated by LED excitation may be too weak to provide an adequate signal-to-noise ratio. An example of a suitable material is the dye platinum (I) tetraphenyl tetrabenzoporphyrin, described in U.S. Pat. No. 6,207,461 to Baumann, which can be excited in the red region. Laser diodes have an added advantage over LEDs in than they generate light having much narrower bands, and narrow bands are desired for light of wavelengths $\lambda_v$ in order to better define the value of the energy $E_v$.

3.2 Alternate Method and Device for the Measurement of Temperature and Oxygen Pressure with a Single Probe Instead of measuring both oxygen pressure and temperature with the same oxygen sensing material as as described in the previous section one may incorporate a second photoluminescent material for measuring temperature, according to the TADA method, within the optical fiber itself near the tip in contact with the oxygen sensing material. Preferably said second material should have optical absorption and luminescence bands different from those of the pressure sensing material. An example of a suitable temperature sensing material is a glass doped with trivalent ytterbium ($Yb^{3+}$). It has a relatively narrow luminescence band at wavelengths near 975 nm, and it can be excited with a relatively inexpensive microlaser at the Nd:YAG laser wavelength of 1.06 micrometers ($\mu$m), in this case the wavelength $\lambda_v$. At this excitation wavelength the value of $E_v$ for $Yb^{3+}$ is approximately 860 $cm^{-1}$. These are widely separated from the excitation and luminescence wavelengths of most oxygen sensing materials. The $Yb^{3+}$-doped glass can be a short silica glass fiber segment fused or otherwise attached to a glass optical fiber guide used for transmitting the excitation lights to the probe.

In a suitable arrangement, the dye platinum(I) tetraphenyl tetrabenzoporphyrin is immobilized within an oxygen-permeable matrix and attached to the tip of an $Yb^{3+}$-doped glass fiber segment fused to a glass optical fiber.

4. Surface Temperature Measurements on Moving Objects

The instant invention makes it possible to measure the surface temperatures of fast moving bodies, for example rotating turbine blades, using as probes efficient phosphors, whether or not they have temperature-dependent luminescence decay times or substantially temperature-dependent luminescence spectral distributions. In the prior art these measurements used as probes paints applied to the surface of said bodies, the paints including a photoluminescent material having a substantially temperature-dependent luminescence decay time $\tau$. The measurements are carried out by exciting the luminescence of the paint with pulses of light of sub-microsecond duration and measuring the luminescence decay. A serious disadvantage of this method is that, in a fast moving body one has to measure the intensities of two short duration fractions of the time-decaying luminescence from the illuminated spot. The first fraction is measured very shortly after the extinction of the excitation pulse, before the peak luminescence intensity has decayed significantly. The second fraction is measured a short interval afterwards, as the spot has moved rapidly away from the position where the intensity of its first luminescence portion was measured. Now, except for a relatively small group of materials described in Kleinerman's U.S. Pat. No. 5,222,810 section 2.0: Luminescent Materials Havinq two Emissive Levels with Temperature-Dependent Relative Populations, a decrease in the luminescence decay time $\tau$ of a probe with increasing temperature parallels a decrease in its luminescence efficiency, which inevitably decreases the signal-to-noise ratio of the measurement. In the high temperature region (above 500° C.) Width which the luminescence decay time $\tau$ decreases appreciably per increasing degree the luminescence quantum efficiencies are often of the order of $10_{-2}$ or smaller. And since only a small fraction of the emitted luminescence intensity is measured, measurement accuracy is limited.

The present invention overcomes these shortcomings and permits the measurement of temperatures and surface temperature distributions with photoluminescent probes which maintain their high luminescence efficiencies over their temperature range of operation and do not require a temperature-dependent change in their luminescence spectral distribution or luminescence efficiency.

For example, $Dy^{3+}$-doped $LuPO_4$ has a luminescence decay time $\tau$ of about 700 microseconds ($\mu$sec) which is essentially constant from ordinary temperatures up to about 1,200K, so it cannot be used as a temperature probe in the decay time mode. Nd:YAG has a luminescence decay time which changes only slowly with increasing temperature over a substantial temperature range. With these photoluminescent materials, the TADA method and its associated instrumentation provides better temperature measuring capabilities, especially within the temperature ranges within which their luminescence decay times do not vary substantially. For example, $Dy^{3+}$ has an electronic energy level $^6H_{13/2}$ about 3,300 $cm^{-1}$ above the $^6H_{15/2}$ ground level, which can be significantly excited thermally at temperatures from about 800K and higher. Light of wavelength $\lambda_v$ of 570 nm excites the $Dy^{3+}$ ions occupying that level to the excited emissive level $^4F_{9/2}$, generating a luminescence intensity with a temperature coefficient greater than 0.5 percent per kelvin below 1,200K. $Nd^{3+}$ ions occupying the thermally excited level $^4I_{11/12}$ can be optically excited, in $Nd^{3+}$-doped phosphors, with light of 1.064 micrometers ($\mu$m) wavelength $\lambda_v$ to the $^4F_{3/2}$ emissive level, or with a $\lambda_v$ of 660 nm to the $^4G_{5/2}$ level. $Eu^{3+}$ ions occupying the thermally excited levels $^7F_2$, $^7F_3$, and $^7F_4$ can be optically excited, in $Eu^{3+}$-doped phosphors, to the emissive level $^5D_0$ with lights of wavelengths of about 612, 650 and 701 nm, respectively, or the $^5D_1$ level with lights of wavelengths of 553, 583 and 626 nm, respectively.

The procedure and associated instrumentation follow essentially the teachings of section 3.1 above for measuring temperature using two excitation lights of wavelengths $\lambda_1$ and $\lambda_v$ as defined therein.

Within the temperature region where the luminescence decay time decreases substantially with an increase in temperature, the TADA method as used according to the invention provides a means for verifying the temperature readings thus obtained with the temperature-dependent luminescence decay time method.

Preferred Embodiments

The preferred embodiments according to the instant invention depend on the desired temperature range of operation. For measuring the temperature of rotating turbine blades, for example, the outer surface of a blade (facing the observer) is coated with a paint containing a phosphor which retains, at the upper end of the working temperature range, no less than about one tenth of its luminescence efficiency at ordinary temperatures. Now, suppose that the turbine rotor is spinning at 15,000 RPM, that is 250 revolutions per second, and that the diameter of the rotor including the blades is 1 meter. The linear velocity of the rotating blade is then $7.85 \times 10^4$ cm/sec. Assume also that a 1 $cm^2$ area of the coated surface near the outer radial edge of the blade is within the fields of view of two excitation light sources and the photodetector. That strip will be under the excitation light for about 12.7 microseconds ($\mu$sec) per revolution. One of the two excitation light sources illuminates said area with light of wavelength $\lambda_1$ as defined above, that is light the absorption of which by the paint has a small or zero temperature dependence, as defined in sections 2 and 3.1 above. This light, of intensity $P_1$, generates a luminescence of intensity $I_1$. The other excitation light source illuminates the same area with light of wavelength $\lambda_v$, the absorption of which is strongly temperature-dependent as defined above. This light has an intensity $P_2$ and generates a luminescence of intensity $I_T$. The paint is illuminated alternately by the two light sources, one for each revolution of the rotor. For each of the two lights, there will be then 125 exposures per second of about 12.7 $\mu$sec_each. The photodetector signals from each of the the luminescence intensities thus generated are integrated for about one second. The temperature of the coated surface is determined from equation (9) above. If the temperature range of operation is from about 600K to about 1000K a suitable phosphor is $Nd^{3+}$-doped yttrium aluminum garnet (Nd:YAG). The wavelength $\lambda_1$ is about 880 nm and excites molecules occupying the ground level $^4I_{9/12}$ to the $^4F_{3/2}$ emissive level. $\lambda_v$ is about 1.064 $\mu$m and excites molecules occupying the thermally excited level $^4I_{11/12}$ to the same $^4F_{3/2}$ emissive level. One of the attractive features of the Nd:YAG phosphor is that both excitation wavelengths are generated by commercially available and relatively inexpensive lasers.

5.0—The Measurement of Surface Temperature Distributions

The prior art for measuring surface temperature distributions uses a temperature sensing paint containing a photoluminescent material applied to the surface on which the temperature distribution is to be measured, and photographic or photo-electronic video imaging techniques. Usually the photoluminescent material has a temperature-dependent luminescence decay time $\tau$. The paint is illuminated with a pulse of luminescence excitation light of much shorter duration than $\tau$. Two successive short time 'slices' of the temperature-dependent luminescence spectral distribution are imaged on and processed by a CCD array or similar photo-electronic imaging device after the excitation light pulse is extinguished, both preferably before the time $\tau$. The relative luminescence intensities from each point at said two time 'slices' give the value of T and, hence, the temperature at each point on the illuminated paint.

In an alternate method one uses a paint including a luminophor having a temperature-dependent luminescence spectral distribution, not necessarily a temperature-dependent luminescence decay time. The paint is illuminated with a CW or pulsed source of luminescence excitation light and the luminescence intensity distribution is focused as an image, through an optical filter that passes only a pre-selected set of wavelengths, on a CCD array or similar digital photo-electronic imaging device. The same luminescence intensity distribution is focused as an image, through another optical filter that passes only a different pre-selected set of wavelengths, on a second photo-electronic imaging device. The relative intensities of the two sets of wavelengths from each point on the coated surface indicate the temperature at that point.

This invention uses a paint wherein the sensing entity is a photoluminescent material dissolved or dispersed therein. The measuring arrangement is substantially similar to the photo-electronic arrangement of the prior art that uses a paint with a photoluminescent material having a temperature-dependent luminescence decay time, except that neither the luminescence decay time, nor the luminescence quantum efficiency nor the luminescence spectral distribution of the photoluminescent material of this invention need be temperature-dependent, provided that the luminescence of said material can be excited by light of wavelength $\lambda_v$ the absorption of which is temperature-dependent as described above. A preferred embodiment uses a temperature sensing paint applied to the surface to be measured. The paint includes a photoluminescent material comprised of a single luminophor. The required area of the paint is illuminated successively by lights of wavelengths $\lambda_1$ and $\lambda_v$ (as defined above), respectively, thus generating luminescence images of distributed intensities $I_1$ and $I_T$, respectively. Two successive luminescence images of the coated surface, one excited by light of wavelength $\lambda_1$ and the second excited by light of wavelength $\lambda_v$, are focused and captured on a digital imaging device, preferably a video camera, digitized and processed by techniques well known in the prior art. The relative luminescence intensities from each and all resolvable smaller areas (pixels) within the illuminated area on the paint excited successively by lights of wavelengths $\lambda_1$ and $\lambda_v$ will be an accurate temperature indicator for said points, whether or not equations (4) to (6) are quantitatively accurate. To the extent that they are, the temperature of each point obeys equation (9) above, regardless of any thickness inhomogeneities in the paint. This can be understood from the following:

One starts from equation (7), where all the factors have been determined by the calibration steps (a) and (b) of section 3.1. We note that for any resolvable smaller area (point) on the luminescent paint, $I_1 = P_1 \cdot \alpha_1 \cdot \phi$. Now, at low optical densities $\alpha_1$ is directly proportional to d, the thickness of the paint at that point. So, keeping in mind that $I_1$ is independent or only minimally temperature-dependent, we can write $$I_1 = K_1 \cdot P_1 \cdot d \cdot \phi$$

and $$I_T = K_2 \cdot P_T \cdot d \cdot \phi \cdot \exp(-E_v/kT)$$

where $K_1$ and $K_2$ are constants. So, dividing $I_T$ by $I_1$ and solving for T one gets equation (9) above, where both the thickness d at each point and the luminescence quantum yield $\phi$ have been canceled out. Therefore, by using two pre-selected excitation wavelengths the temperature at each point over the paint is determined unambiguosly regardless of any thickness variations.

To summarize, successive illuminations of the paint with lights of wavelengths $\lambda_1$ and $\lambda_v$ generate luminescence distributions of intensities $I_1$ and $I_T$, respectively, at any and all said resolvable smaller areas (pixels), in such a manner that the ratio $(I_T \cdot P_1/I_1 \cdot P_T)$ for each of said points increases substantially in a known manner with increasing temperature; substantially independent of any air pressure then acting on the paint or of any thickness inhomogeneities on it.

5.1—The Measurement of Temperature Distributions on the Surface of Moving Objects For measuring temperature distributions on the surface of moving objects one may use the same technique described in the preceding paragraphs, with the added proviso that the two successive luminescence images of the coated surface, one excited by light of wavelength $\lambda_1$ and the second excited by light of wavelength $\lambda_v$, are obtained while the moving surface is within the field of view of the light sources and the exposures are short enough that image is not blurred. The task is greatly simplified if the moving object is part of a fast revolving structure, like rotating turbine blades, because a large number of reproducible single exposures short enough to 'freeze' the motion can be integrated in order to increase the signal-to-noise ratio for each pixel.

6.—An Alternate Method for Measuring Surface Temperature Distributions

Some photoluminescent materials have at least two excited emissive levels having an energy difference $E_e$ such that, if the lower of these emissive levels has a relatively long decay time t (typically of the order of $10^{-4}$ seconds or longer) and is populated by optical excitation of molecules from the ground level, the molecules so excited distribute themselves between these two levels approximately as a function of the Boltzmann factor $\exp(-E_e/kT)$, where k is the Boltzmann constant and T is the absolute temperature in kelvins, as defined above. These two excited levels are referred to herein as being in a Boltzmann equilibrium. Examples of such systems were described in Kleinerman's U.S. Pat. No. 5,222,810 section 2.0: Luminescent Materials Having two Emissive Levels with Temperature-Dependent Relative Populations. If the rate of radiative decay from the higher excited level is not lower than that from the lower excited level, the luminescence intensity emitted from the higher level increases relative to that of the lower emissive level, and the spectral distribution of the total luminescence is changed. And if the probe is a paint, the relative intensities of the luminescence bands originating from the two emissive levels is an unambiguous temperature indicator, regardless of thickness variations at different sensing points.

One kind of photoluminescent materials having at least two excited emissive levels in a Boltzmann equilibrium are some $Cr^{3+}$-doped inorganic crystals wherein the excited emissive level $^4T_2$ level lies above the $^2E$ excited emissive level so that, upon absorption of light that excites either of these levels, there is a temperature range within which there is thermal excitation of molecules in the $^2E$ level to the $^4T_2$ level so that intensity of the luminescence spectral band originating at the $^4T_2$ level increases with increasing temperature at the expense of the intensity of the luminescence spectral band originating at the $^2E$ level.

Another kind of photoluminescent materials having at least two excited emissive levels in a Boltzmann equilibrium are some rare earth-doped inorganic crystals and glasses. For example, the trivalent neodymium ion $Nd^{3+}$ has a lower excited emissive level $^4F_{3/2}$ separated by an energy of about 1080 $cm^{-1}$ from the higher emissive level $^4F_{5/2}$. At temperatures above 800K (527° C.) the luminescence emission band at about 810 nanometers (nm) from the $^4F_{5/2}$ to the ground level $^4I_{9/2}$ becomes quite evident and its intensity increases relative to the luminescence intensity from the $^4F_{3/2}$ level. Temperature readings can be derived, then, from the temperature-dependent spectral distribution of the luminescence.

The invention subject of Kleinerman's U.S. Pat. No. 5,222,810 is limited to the measurement of spot temperatures. The instant invention is an improvement and extension of the concept of the Boltzmann equilibrium between two excited luminescent levels to the measurement of surface temperature distributions. Furthermore, it provides a means for verifying the temperature readings thus obtained with the independent luminescence intensities obtained from the TADA readings. If the photoluminescent material in a temperature sensing paint is chosen from the group of materials having at least two excited emissive levels in a Boltzmann equilibrium, then the temperature readings obtained from the luminescence decay time $\tau$ and/or the temperature-dependent spectral distribution of the luminescence can be checked and validated with the temperature readings obtained from equation (9) of the TADA technology.

7.—The Measurement of Surface Temperature and Air Pressure Distributions with a Single Coating It was shown in section 5.0 above that the use of alternating illumination with lights of two different sets of wavelengths $\lambda_1$ and $\lambda_v$ allows accurate temperature measurements regardless of thickness variations. It should be apparent that other inhomogeneities are also canceled out.

The determination of air pressure distributions in the presence of temperature or other physical variables affecting the photoluminescent paint can be effected by measuring the oxygen-dependent luminescence decay time of the photoluminescent material. This requires, if not a perfectly homogeneous paint, at least a calibration of the actual paint. This can be effected by applying as homogeneous a paint as practical (without very laborious and/or 'heroic' efforts), keeping the painted surface at a homogeneous temperature in an oxygen-free environment, and illuminating it with a light beam of wavelength or wavelengths $\lambda_1$ which is homogeneous over the tested area of the paint. Any luminescence intensity variations over the paint will be due to inhomogeneities on the paint itself. From these luminescence intensity variations one can determine the correction factors to be applied at each and all points.

In practice, the luminescence intensity variations over the painted area (which are generated not only by temperature and/or air pressure distributions but also by any present paint inhomogeneities present) are recorded as a luminescence image by digital cameras and computer-processed. The number of exposures depends, inter alia, on the nature of the paint used, and on whether the surface is stationary or moving rapidly.

The procedure and arrangement for measuring surface temperature and air pressure distributions follows clearly from the teachings of sections 3.0, 3.1 and 5.0 above. A coating (paint) containing a photoluminescent material having an oxygen-sensitive luminescence decay time $\tau$ is applied to the surface of interest. The coating has been calibrated as described in section 3.1 above. In a preferred embodiment the air pressure and temperature distributions are obtained as follows:

(1) The paint is excited with a short, intense pulse of light of wavelength or wavelengths $\lambda_1$ (which is absorbed by the photoluminescent material with little or no temperature dependence) and known intensity $P_1$. The pulse duration is preferably more than an order of magnitude shorter than about the average of the distributed decay times of the luminescence under the air pressures being measured, said average designated herein as $\tau_{av}$.

(2) At a pre-selected time t after the excitation light pulse has been extinguished, but beginning before a time of about $0.3\tau_{av}$ has elapsed, the first of two successive short time 'slices' of the time-decaying luminescence intensity distributions (images), each of duration $\Delta t$ shorter than $0.5\tau_{av}$, is focused on and processed by a digital video device, followed by the second time 'slice'. The relative luminescence intensities from each point at said two luminescence images give the value of $\tau$ each point on the illuminated paint.

(3) The luminescence spatial distribution of the first time 'slice' is saved and stored.

(4) Now the paint is excited with a short, intense pulse of light of wavelength or wavelengths $\lambda_v$ (the absorption of which by the photoluminescent material is substantially temperature-dependent), known intensity $P_1$, and the same duration as that of the light pulse of wavelength $\lambda_1$.

(5) At the same pre-selected time t after the excitation light pulse has been extinguished, a time 'slice' of the luminescence image generated by said pulse of light of wavelength or wavelengths $\lambda_v$, of the same duration $\Delta t$ as that of the first time 'slice' of the luminescence excited by the light pulse of wavelength $\lambda_1$, is focused on and processed by the same or an identical digital video device.

(6) For each point on the photoluminescent paint, the relative luminescence signals generated by the excitation lights of wavelengths $\lambda_1$ and $\lambda_v$ and processed by the digital video device(s) define the temperature at that point according to equation (9) (section 2, supra). The temperature data for each point are applied to the t values obtained in step (2), thus providing a temperature compensation factor for converting each $\tau$ value at each point on the paint surface to a true air pressure.

Since changes may be made in the foregoing disclosure without departing from the scope of the invention herein involved, it is intended that all matter contained in the above description and depicted in the accompanying drawings be construed in an illustrative and not in a limiting case.

I claim:

1. A method for measuring the temperature of an object or environment with a photoluminescent probe, comprising the steps of:

a) providing a probe in thermal communication with said object or environment, said probe including a photoluminescent material so characterized that, when illuminated at any temperature within the temperature range of application of the method with a first excitation light of intensity $P_1$ and pre-selected wavelength or wavelengths $\lambda_1$, it emits a first luminescence light of intensity $I_1$, and when illuminated with a second excitation light of intensity $P_T$ and pre-selected wavelength or wavelengths $\lambda_v$, it emits a second luminescence light of intensity $I_T$ so related to the luminescence intensity $I_1$ that the ratio $(I_T \cdot P_1 / I_1 \cdot P_T)$ increases substantially in a known manner with increasing temperature;

b) illuminating said material with said first excitation light of said wavelength or wavelengths $\lambda_1$ and intensity $P_1$, thereby generating a first luminescence light emitted by the probe with said intensity $I_1$;

c) directing a fraction of said intensity $I_1$ of said first luminescence light to photodetector means;

d) illuminating said material, subsequently to its illumination with said first excitation light, with said second excitation light of an intensity $P_T$ and wavelength or wavelengths $\lambda_v$, thereby generating a second luminescence light emitted by the probe having an intensity $I_T$;

e) directing a fraction of said intensity $I_T$ of said second luminescence light to photodetector means; and f) measuring the relative intensities of the luminescence lights generated by said first and said second excitation lights received by said photodetector means, said relative intensities being an indicator of the temperature being measured.

2. A method as claimed in claim 1 wherein said probe is attached to the distal end of an optical fiber light guide having a proximal end and a terminal end; said first and second excitation lights are injected into the optical fiber light guide at or near its proximal end, and said fractions of the intensities of said first and said second luminescence lights are directed by said optical fiber light guide to said photodetector means, said photodetector means being located near the proximal end of said optical fiber light guide.

3. A method as claimed in claim 1 and adapted to measure oxygen pressure in addition to temperature, wherein said photoluminescent material is additionally so characterized that, when excited with a pulsed or AC-modulated light of wavelength or wavelengths $\lambda_1$ at any temperature within the useable temperature range of application of the method, it emits a luminescence light with a decay time $\tau$ which decreases in a known manner with increasing oxygen pressure, the method additionally comprising the steps of exciting said material with said pulsed or AC-modulated light and measuring said luminescence decay time, said decay time being an indicator of said optical pressure at the measured temperature.

4. A method as claimed in claim 3 wherein said probe is attached to the distal end of an optical fiber light guide having a proximal end and a terminal end; said first and second excitation lights and said pulsed or AC-modulated light are injected into the optical fiber light guide at or near its proximal end, and said luminescence lights are directed by said optical fiber light guide to said photodetector means, said photodetector means being located near the proximal end of said optical fiber light guide.

5. A method as claimed in claim 3 wherein said photoluminescent material is comprised of a single luminophor.

6. A method as claimed in claim 1 adapted for measuring temperature distributions on a surface covered by a photoluminescent paint, wherein said first excitation light of intensity $P_1$ and wavelength or wavelengths $\lambda_1$ and said second excitation light of intensity $P_T$ and wavelength or wavelengths $\lambda_v$ successively illuminate a selected area of said paint, said area comprising a multiplicity of resolvable smaller areas, thus generating at said selected area, a distribution of first luminescence lights of intensities $I_1$ and second luminescence lights of intensities $I_T$, the luminescence intensities at each of said smaller areas being so related that said ratio $(I_T \cdot P_1 / I_1 \cdot P_T)$ increases substantially in a known manner with increasing temperature, the method additionally comprising the steps of a) capturing and digitizing, by a digital video device, said distribution of luminescence intensities $I_1$ caused by said first excitation light of wavelength or wavelengths $\lambda_1$ at the surface of said paint;

b) capturing and digitizing, by a digital video device, said distribution of luminescence intensities $I_T$ caused by said second excitation light of wavelength or wavelengths $\lambda_v$ at the surface of said paint; and c) determining the temperatures of said smaller areas from said ratio $(I_T \cdot P_1 / I_1 \cdot P_T)$.

7. A method for measuring temperature distributions on a photoluminescent paint as claimed in claim 6, wherein said paint is a pressure-sensitive paint, and said temperature distributions determined as recited in claim 6 are substantially independent of any air pressure then acting on the paint or of any thickness inhomogeneities on the paint.

8. A method for measuring air pressure and temperature distributions on a photoluminescent paint, comprising the steps as recited in claim 6, wherein said paint contains a photoluminescent material so characterized that when illuminated with a short pulse of light of said wavelength or wavelengths $\lambda_1$ or any other suitable wavelength or wavelengths at any temperature within the useable temperature range of application of the method, it emits a luminescence light with a decay time $\tau$ which decreases in a known manner with increasing air pressure, the method additionally comprising the steps of a) illuminating said selected area of said paint with an excitation light pulse of duration shorter than $\tau$ and suitable wavelength or wavelengths, thereby generating at said smaller areas on the illuminated paint a luminescence light of distributed intensities and distributed decay times $\tau$, b) capturing and digitizing, after said excitation light pulse is extinguished, said distributed intensities generated by said light pulse by a digital video system at at least two successive non-overlapping time periods shorter than the average $\tau_{av}$ of said distributed decay times, the relative luminescence intensities from each smaller area during said successive time periods determining the value of $\tau$ at each of said smaller areas on the illuminated paint; and c) determining the decay times of the luminescence from each of said smaller areas from the relative luminescence intensities from said smaller areas at each of said two successive time periods; and d) determining the air pressures on said smaller areas from their luminescence decay times.

9. An arrangement for measuring the temperature of an object or environment, comprising a) a probe in thermal communication with said object or environment, said probe including a photoluminescent material so characterized that, when illuminated at any temperature within the temperature range of application of the arrangement with a first excitation light of intensity $P_1$ and pre-selected wavelength or wavelengths $\lambda_1$, it emits a first luminescence light of intensity $I_1$, and when illuminated with a second excitation light of intensity $P_T$ and pre-selected wavelength or wavelengths $\lambda_v$, it emits a second luminescence light of intensity $I_T$, the relative responses of the luminescence intensities $I_T$ and $I_1$ to a temperature change being such that the ratio $(I_T \cdot P_1 / I_1 \cdot P_T)$ increases substantially in a known manner with increasing temperature;

b) first light source means for illuminating said material with said first excitation light of said wavelength or wavelengths $\lambda_1$ and intensity $P_1$, and thus generating a first luminescence light emitted by the probe with said intensity $I_1$;

c) second light source means for illuminating said material with said second excitation light of an intensity $P_T$ and wavelength or wavelengths $\lambda_v$, thereby generating a second luminescence light emitted by the probe having an intensity $I_T$;

d) optical means for directing a fraction of said intensity $I_1$ of said first luminescence light to photodetector means;

e) optical means for directing a fraction of said intensity $I_T$ of said second luminescence light to photodetector means; and f) photodetector and associated electronic means for measuring the relative intensities of the luminescence lights generated by said first and said second excitation lights received by said photodetector means, said relative intensities being an indicator of the temperature being measured.

10. An arrangement as claimed in claim 9 wherein said probe is attached to the distal end of an optical fiber light guide having a proximal end and a terminal end; said first and said second excitation light source means are configured to inject said first and said second excitation lights into the optical fiber light guide at or near its proximal end; said optical fiber light guide is provided with optical pathways for directing fractions of the intensities of said first and said second luminescence lights to said photodetector means, said photodetector means being located near the proximal end of said optical fiber light guide.

11. An arrangement as claimed in claim 9 wherein said probe is a coating applied to the surface of said object or part thereof.

12. An arrangement as claimed in claim 10 and adapted to measure oxygen pressure in addition to temperature, wherein said photoluminescent material is additionally so characterized that, when excited with a pulsed or AC-modulated light of wavelength or wavelengths $\lambda_1$ at any temperature within the useable temperature range of application of the arrangement, it emits a luminescence light with a decay time $\tau$ which decreases in a known manner with increasing oxygen pressure, the arrangement additionally comprising the light source means for exciting the luminescence of said material with said pulsed or AC-modulated light and for measuring said luminescence decay time, said decay time being an indicator of said optical pressure at the measured temperature.

13. An arrangement as claimed in claim 12 wherein said probe is attached to the distal end of an optical fiber light guide having a proximal end and a terminal end; said first and said second excitation light source means and said pulsed or AC-modulated light source means are configured to inject into the optical fiber light guide at or near its proximal end, and said luminescence lights are directed by said optical fiber light guide to said photodetector means, said photodetector menas being located near the proximal end of said optical fiber light guide.

14. An arrangement as claimed in claim 12 wherein said photoluminescent material is comprised of a single luminophor.

15. An arrangement for measuring the temperature distribution on a surface covered by a photoluminescent paint, comprising a) first light source means for illuminating a selected area of said paint, said area comprising a multiplicity of resolvable smaller areas, with a first excitation light of wavelength or wavelengths $\lambda_1$ and intensity $P_1$, so chosen that it generates a luminescence image at said selected area, said image comprised of the luminescence intensities $I_1$ of each and all said smaller areas;

b) optical means for focusing and storing said luminescence image on a video image device;

c) second light source means for illuminating said selected area of said paint with said second excitation light of an intensity $P_T$ and wavelength or wavelengths $\lambda_v$ so chosen that it generates a luminescence image at said selected area, said image comprised of the luminescence intensities $I_T$ of each and all said smaller areas, the intensity at any of said smaller areas being related to the luminescence intensity $I_1$ at the same smaller area in such a manner that the ratio $(I_T \cdot P_1/I_1 \cdot P_T)$ increases substantially in a known manner with increasing temperature; substantially independent of any air pressure then acting on the paint or of any thickness inhomogeneities on the paint;

d) optical means for focusing and storing said luminescence image generated by said second excitation light on a video image device;

e) electronic means for computing said ratio $(I_T \cdot P_1/I_1 \cdot P_T)$ for each and all said resolvable smaller areas and thus determining the temperature distribution at said surface.

16. An arrangement for measuring temperature distributions on a photoluminescent paint as claimed in claim 15, wherein said paint is a pressure-sensitive paint, and said temperature distributions determined as recited in claim 15 are substantially independent of any air pressure then acting on the paint or of any thickness inhomogeneities on the paint.

\* \* \* \* \*